United States Patent [19]

Chan

[11] 4,372,972
[45] Feb. 8, 1983

[54] N-SUBSTITUTED ALKYNYL ANILINES

[75] Inventor: Hak-Foon Chan, Doylestown, Pa.

[73] Assignee: Rohm and Haas Company, Philadelphia, Pa.

[21] Appl. No.: 75,563

[22] Filed: Sep. 14, 1979

[51] Int. Cl.$^3$ ............... A01N 37/22; C07C 103/737
[52] U.S. Cl. ................ 424/304; 260/465 D; 424/285; 424/309; 424/324; 549/487; 560/10; 560/12; 560/13; 560/16; 560/21; 560/22; 560/41; 560/42; 560/43; 564/123; 564/184; 564/192; 564/194; 564/202; 564/207
[58] Field of Search ............ 260/347.2, 347.3, 347.4, 260/465 D, 557 R, 558 A, 558 DP, 559 R, 562 R, 562 N, 562 S, 562 B, 562 P, 562 A; 560/43; 424/285, 304, 309, 324; 564/123, 184, 192, 194, 202, 207

[56] References Cited

U.S. PATENT DOCUMENTS

| | | | |
|---|---|---|---|
| 3,268,583 | 8/1966 | Moore et al. | 260/562 R X |
| 3,442,945 | 5/1969 | Olin | 260/562 |
| 3,475,156 | 10/1970 | Olin | 71/118 |
| 3,475,157 | 10/1969 | Olin | 71/118 |
| 3,535,377 | 10/1970 | Steinbrunn | 260/562 |
| 3,839,415 | 10/1974 | Easton et al. | 260/562 R X |
| 4,001,325 | 1/1977 | Bluestone et al. | 260/562 |
| 4,013,684 | 3/1977 | Merkle et al. | 260/347.3 |
| 4,021,224 | 5/1977 | Pallos et al. | 260/347.3 V |
| 4,275,079 | 6/1981 | Dorn | 424/324 |

OTHER PUBLICATIONS

Makisumi et al., Chem. Pharm. Bull., vol. 24, No. 4 (1976), pp. 770-777.

Primary Examiner—Richard Raymond
Attorney, Agent, or Firm—George W. F. Simmons; Alex R. Sluzas; Polly E. Ramstad

[57] ABSTRACT

This invention relates to N-substituted alkynyl anilines, methods for their preparation and their use as systemic eradicant phytopathogenic fungicides which are useful in controlling Oömycetes.

8 Claims, No Drawings

N-SUBSTITUTED ALKYNYL ANILINES

BACKGROUND OF THE INVENTION

It is known in the art that N-substituted alkynyl anilines having haloacetyl substituents attached to the nitrogen atom of the aniline group possess herbicidal activity. This disclosure can be found in U.S. Pat. No. 3,475,156 granted Oct. 28, 1969; U.S. Pat. No. 3,475,157 granted Oct. 28, 1969; U.S. Pat. No. 3,535,377 granted Oct. 20, 1970 and U.S. Pat. No. 4,001,325 granted Jan. 4, 1977. The present invention relates to N-substituted alkynyl anilines which are unexpectedly effective against Oömycetes in agronomic crops. These compounds in addition to their ability to control these phytopathogenic fungi possess systemic/eradicant activity as well.

SUMMARY OF THE INVENTION

This invention relates to N-substituted alkynyl anilines of the formula

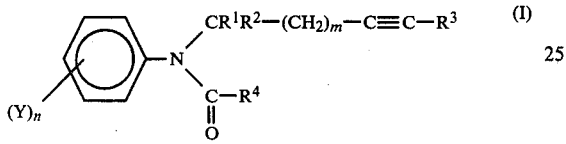

wherein
$R^1$, $R^2$ and $R^3$ are independently hydrogen, $(C_1-C_4)$alkyl, $(C_2-C_4)$alkenyl, $(C_2-C_4)$alkynyl, $(C_3-C_8)$cycloalkyl, $(C_5-C_8)$cycloalkenyl, halogen, cyano, carbo$(C_1-C_{10})$alkoxy aryl or aryl$(C_1-C_4)$alkyl, the aryl portion of which is optionally substituted;
$R^4$ is $(C_2-C_4)$alkenyl, $(C_2-C_4)$alkynyl, $(C_3-C_8)$cycloalkyl, $(C_5-C_8)$cycloalkenyl, optionally substituted aryl, 2-furanyl, 2-tetrahydrofuranyl, $(C_1-C_6)$alkoxy$(C_1-C_3)$alkyl, $(C_1-C_6)$alkylthio$(C_1-C_3)$alkyl, or mono or di$(C_1-C_6)$alkylamino$(C_1-C_3)$alkyl, $(C_2-C_6)$alkenyloxy$(C_1-C_3)$alkyl, $(C_2-C_6)$alkenylthio$(C_1-C_3)$alkyl, mono or di$(C_2-C_6)$alkenylamino$(C_1-C_3)$alkyl, $(C_2-C_6)$alkynyloxy$(C_1-C_3)$alkyl, $(C_2-C_6)$alkynylthio$(C_1-C_3)$alkyl, mono or di$(C_2-C_6)$alkynylamino$(C_1-C_3)$alkyl, or halocarbonyl;
Y is halogen, $(C_1-C_4)$alkyl, $(C_1-C_4)$alkoxy, nitro, mono or di$(C_1-C_4)$alkylamino, trihalomethyl, cyano, phenyl, phenoxy, phenylthio, phenylsulfinyl or phenylsulfonyl optionally substituted with up to three substituents;
m and n are independently zero or an integer from 1 to 3;
methods for their preparation and their use as systemic/eradicant phytopathogenic fungicides particularly useful in controlling Oomycetes diseases in agronomic crops at rates of application below 2,000 ppm.

DETAILED DESCRIPTION OF THE INVENTION

This invention relates to N-substituted alkynyl anilines of Formula (I) wherein
$R^1$, $R^2$ and $R^3$ are independently hydrogen, $(C_1-C_4)$alkyl, $(C_2-C_4)$alkenyl, $(C_2-C_4)$alkynyl, $(C_3-C_8)$cycloalkyl, $(C_5-C_8)$cycloalkenyl, halogen, cyano, carbo$(C_1-C_{10})$alkoxy, phenyl or phenyl$(C_1-C_4)$alkyl optionally substituted with up to three substituents independently selected from the group consisting of halogen, $(C_1-C_4)$alkyl, $(C_1-C_4)$alkoxy, nitro, $(C_1-C_4)$alkylamino or di$(C_1-C_4)$alkylamino, trihalomethyl or cyano;
$R^4$ is $(C_2-C_6)$alkenyl, $(C_2-C_6)$alkynyl, $(C_3-C_8)$cycloalkyl, $(C_5-C_8)$cycloalkenyl, optionally substituted aryl, 2-furanyl, 2-tetrahydrofuranyl, $(C_1-C_6)$alkoxy$(C_1-C_3)$alkyl, $(C_1-C_6)$alkylthio$(C_1-C_3)$alkyl, mono or di$(C_1-C_6)$alkylamino$(C_1-C_3)$alkyl, $(C_2-C_6)$alkenyloxy$(C_1-C_3)$alkyl, $(C_2-C_6)$alkenylthio$(C_1-C_3)$alkyl, mono or di$(C_2-C_6)$alkenylamino$(C_1-C_3)$alkyl, $(C_2-C_6)$alkynyloxy$(C_1-C_3)$alkyl, $(C_2-C_6)$alkynylthio$(C_1-C_3)$alkyl, mono or di$(C_2-C_6)$alkynylamino$(C_1-C_3)$alkyl, or halocarbonyl;
Y is halogen, $(C_1-C_4)$alkyl, $(C_1-C_4)$alkoxy, nitro, $(C_1-C_4)$alkylamino or di$(C_1-C_4)$alkylamino, trihalomethyl, cyano, phenyl, phenoxy, phenylthio, phenylsulfinyl, or phenylsulfonyl optionally substituted with up to three substituents independently selected from the group consisting of halogen, $(C_1-C_4)$alkyl, $(C_1-C_4)$alkoxy, nitro, $(C_1-C_4)$alkylamino or di$(C_1-C_4)$alkylamino, trihalomethyl and cyano;
m and n independently are zero or an integer from 1 to 3.

The terms "alkyl", "alkenyl" and "alkynyl" as utilized in the present specification and claims is meant to encompass both branched and straight chain groups unless specifically defined otherwise. The term "optionally substituted aryl" and as utilized in the present specification and claims is meant to encompass both phenyl and naphthyl groups, preferably a phenyl group, which can be substituted with up to three substituents independently selected from the group consisting of halogen, $(C_1-C_4)$alkyl, $(C_1-C_4)$alkoxy, nitro, $(C_1-C_4)$alkylamino or di$(C_1-C_4)$alkylamino, trihalomethyl, cyano and the like.

Typical compounds encompassed by the present invention include:
N-(3-butynyl)-N-(methoxyacetyl)-2,6-dimethylbenzenamine
N-(2-butynyl)-N-(2-furoyl)-2,6-dimethylbenzenamine
N-(Methoxyacetyl)-N-(2-methyl-3-butyn-2-yl)-2,6-dimethylbenzenamine
N-(Cyclopropylcarbonyl)-N-(1-ethynylcyclopropyl)-2,6-dimethylbenzenamine
N-(Methylthioacetyl)-N-(2-propynyl)-2-chloro-6-methylbenzenamine
N-(Dimethylaminoacetyl)-N-(2-propynyl)-2,6-dimethyl-4-trifluoromethylbenzenamine
N-(1-cyano-2-propynyl)-N-(cyclopentylcarbonyl)-2-ethyl-6-methylbenzenamine
N-(3-Carbomethoxy-2-propynyl)-N-(methoxyacetyl)-2,6-dimethyl-4-nitrobenzenamine
N-(2-Chloro-1,2-dioxethyl)-N-(2-propynyl)-2,6-dimethylbenzenamine
N-(Benzoyl)-N-(3-phenylpropynyl)-2,4,6-trimethylbenzenamine
N-(4-Carboethoxy-2-methyl-3-butyn-2-yl)-N-(methoxyacetyl)-4-phenoxybenzenamine
N-(2-Methylpropenoyl)-N-(2-propynyl)-2,6-dinitrobenzenamine
N-(2-Methylpropenoyl)-N-(2-propynyl)-2,6-dimethylbenzenamine
N-(3-Butyn-2-yl)-N-(propynoyl)-2,4,6-trimethylbenzenamine N-(2-Butynoyl)-N-(2-propynyl)-2,6-dimethylbenzenamine A preferred process of this invention relates to compounds of Formula (I) wherein $R^1$, $R^2$ and $R^3$ are independently hydrogen or ($C_1$-$C_4$)alkyl;

$R^4$ is ($C_2$-$C_4$)alkenyl, ($C_2$-$C_4$)alkynyl, cyclopropyl, cyclopentyl, cyclohexyl, cyclohexenyl, phenyl, 2-furanyl, 2-tetrahydrofuranyl, methoxymethyl, ethoxymethyl, methylthiomethyl, ethylthiomethyl, ethylaminomethyl, dimethylaminomethyl, ethylaminomethyl, diethylaminoethyl, aryloxymethyl, propargyloxymethyl, allylaminomethyl and propargylaminomethyl, or halocarbonyl;

Y is halogen, ($C_1$-$C_4$)alkyl, ($C_1C_4$)alkoxy, nitro, trifluoromethyl, phenyl, phenoxy, phenylthio, phenylsulfinyl, phenylsulfonyl the phenyl portion of which is optionally substituted with up to two halogen atoms, methyl, methoxy, nitro or trifluoromethyl groups;

m is zero; and n is zero or the integer 1 or 2.

The compounds of the present invention can be prepared by routine synthetic routes. In addition thereto, these compounds can be prepared by the following reaction sequence

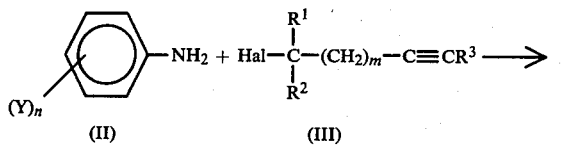

In this reaction a suitably substituted aniline of Formula (II) and a haloalkyne of Formula (III) are reacted in a suitable organic solvent in the presence of an acid scavenger to give an N-alkynyl aniline of Formula (IV). The N-alkynyl aniline of Formula (IV) is then reacted with an acid halide of Formula (V) in the presence of an acid scavenger in a suitable organic solvent to provide the desired product of Formula (I).

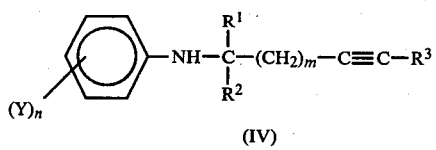

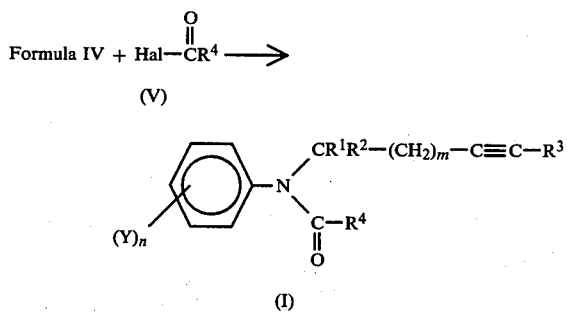

Suitable solvents which can be employed in the above reactions are hydrocarbons such as toluene, xylene, and the like; ethers such as diethylether, tetrahydrofuran and the like; and halogenated hydrocarbons such as methylene chloride, chloroform and the like.

Acid scavengers commonly employed in the above reactions include triethylamine, sodium hydroxide, sodium or potassium carbonate, sodium or potassium bicarbonate, molecular sieves and the like. Reaction temperatures which can be utilized in the above process are temperatures from about 0° to about 100° C.

The appropriately substituted anilines of Formula II can be prepared by standard synthetic routes described in the literature or are commercially available materials.

EXAMPLE 1

Preparation of
N-(2-furoyl)-N-(2-propynyl)-2,6-dimethylbenzenamine

A. N-(2-propynyl)-2,6-dimethylbenzenamine

A mixture of 21.8 g (0.18 mole) of 2,6-dimethylaniline and 21.2 g (0.2 mole) sodium carbonate in 100 ml of ethanol is heated to reflux and stirred rapidly as 23.5 g (0.2 mole) of propargyl bromide, dissolved in 50 ml of ethanol, is added dropwise over a period of 1.5 hr. Upon completing the addition of propargyl bromide the mixture is heated to reflux for one hour and then cooled to room temperature. The reaction mixture is poured into 250 ml of ether and then washed with water (2×100 ml) and brine (100 ml). The washed mixture is dried over anhydrous sodium sulfate, filtered, and the solvent removed under reduced pressure to yield 25.2 g of a red oil. This oil is vacuum distilled through a 6" column to yield 20.0 g (0.13 mole) of N-(2-propynyl)-2,6-dimethylbenzenamine (b.p.=69°–75° C. at 0.75 mm Hg) as a slightly yellow oil.

B. N-(2-furoyl)-N-(2-propynyl)-2,6-dimethylbenzenamine

A mixture of 3.64 g (0.025 mole) of N-(2-propynyl)-2,6-dimethylbenzenamine and 2.52 g (0.025 mole) of triethylamine in 25 ml of dichloromethane is stirred rapidly under nitrogen at room temperature as 3.06 g (0.025 mole) of 2-furoyl chloride, dissolved in 5 ml of dichloromethane, is added at a moderate rate. Upon addition of the 2-furoyl chloride a vigorous exotherm is noted, causing the solvent to reflux for 2 min. The mixture is stirred for 30 min. and then poured into 200 ml of dichloromethane and washed with water (100 ml), 5% HCl (100 ml), water (100 ml) and brine (100 ml). The organic layer is dried over anhydrous sodium sulfate, filtered and the solvent removed under reduced pressure to yield a solid. The solid is washed with n-hexane and vacuum dried to yield 3.65 g (0.0144 mole) of N-(2-furoyl)-N-(2-propynyl)-2,6-dimethylbenzenamine.

nmr (CDCl$_3$): δ7.4 (broad singlet, 1H), 7.2–7.0 (broad singlet, 3H), 6.2–6.0 (m, 1H), 5.5 (d, 1H), 4.5 (d, 2H), 2.2 (S, 7H).

EXAMPLE 2

Preparation of
N-(2-Methoxyacetyl)-N-(2-propynyl)-2,6-dimethylbenzenamine

A mixture of 3.18 g (0.02 mole) of N-(2-propynyl)-2,6-dimethylbenzenamine, 2.4 g (0.022 mole) of methoxyacetyl chloride and 6 g of 4A molecular sieves in 100 ml of toluene is stirred at 60° overnight under a nitrogen atmosphere. The reaction mixture is cooled to room temperature and then filtered. The filtrate is combined with 200 ml of ether and washed with water, saturated sodium chloride solution, and dried over sodium sulfate. The drying agent is filtered and the solvent is evaporated under vacuum to give an orange-red oily material which is further purified by column chromatography (silica gel) using 20/80 ethyl acetate-n-hexane as solvent to give 2.57 g of pure product.

nmr (CDCl$_3$): δ7.19 (S, 3H), 4.45 (d, 2H), 3.58 (S, 2H), 3.35 (S, 3H), 2.35 (Singlet with a small shoulder, 7H).

Tables I and II give the structure, melting points in degrees centigrade and the elemental analysis of some of the more representative compounds encompassed by the present invention which were synthesized by the above procedures.

TABLE I

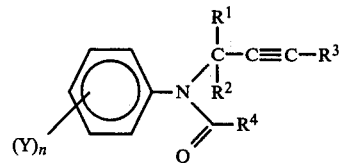

| Example No. | Formula | (Y)$_n$ | R$^1$ | R$^2$ | R$^3$ | R$^4$ |
|---|---|---|---|---|---|---|
| 1 | C$_{16}$H$_{15}$NO$_2$ | 2,6-(CH$_3$)$_2$ | H | H | H | furyl |
| 2 | C$_{14}$H$_{17}$NO$_2$ | 2,6-(CH$_3$)$_2$ | H | H | H | CH$_2$OCH$_3$ |
| 3 | C$_{18}$H$_{19}$NO$_2$ | 2,6-(C$_2$H$_5$)$_2$ | H | H | H | furyl |
| 4 | C$_{16}$H$_{21}$NO$_2$ | 2,6-(C$_2$H$_5$)$_2$ | H | H | H | CH$_2$OCH$_3$ |
| 5 | C$_{16}$H$_{15}$NO$_2$ | 2,4-(CH$_3$)$_2$ | H | H | H | furyl |
| 6 | C$_{14}$H$_{17}$NO$_2$ | 2,4-(CH$_3$)$_2$ | H | H | H | CH$_2$OCH$_3$ |
| 7 | C$_{15}$H$_{17}$NO | 2,4-(CH$_3$)$_2$ | H | H | H | cyclopropyl |
| 8 | C$_{16}$H$_{15}$NO$_2$ | 2,5-(CH$_3$)$_2$ | H | H | H | furyl |
| 9 | C$_{14}$H$_{17}$NO$_2$ | 2,5-(CH$_3$)$_2$ | H | H | H | CH$_2$OCH$_3$ |
| 10. | C$_{15}$H$_{17}$NO | 2,5-(CH$_3$)$_2$ | H | H | H | cyclopropyl |
| 11. | C$_{18}$H$_{17}$NO | 2,5-(CH$_3$)$_2$ | H | H | H | phenyl |
| 12. | C$_{17}$H$_{17}$NO$_2$ | 2,4,6-(CH$_3$)$_3$ | H | H | H | furyl |
| 13. | C$_{15}$H$_{19}$NO$_2$ | 2,4,6-(CH$_3$)$_3$ | H | H | H | CH$_2$OCH$_3$ |
| 14. | C$_{16}$H$_{19}$NO | 2,4,6-(CH$_3$)$_2$ | H | H | H | cyclopropyl |
| 15. | C$_{19}$H$_{19}$NO | 2,4,6-(CH$_3$)$_3$ | H | H | H | phenyl |
| 16. | C$_{15}$H$_{17}$NO$_2$ | 2,4-(CH$_3$)$_2$ | H | H | H | C(CH$_3$)=CH$_2$ |
| 17. | C$_{13}$H$_{15}$NO$_2$ | 2-CH$_3$ | H | H | H | CH$_2$OCH$_3$ |

TABLE I-continued

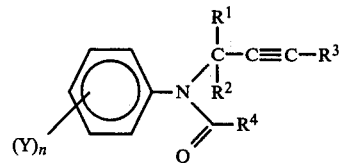

| Example No. | Formula | (Y)$_n$ | R$^1$ | R$^2$ | R$^3$ | R$^4$ |
|---|---|---|---|---|---|---|
| 18. | C$_{15}$H$_{13}$NO$_2$ | 2-CH$_3$ | H | H | H | furyl |
| 19. | C$_{15}$H$_{17}$NO | 2,6-(CH$_3$)$_2$ | H | H | H | cyclopropyl |

TABLE II

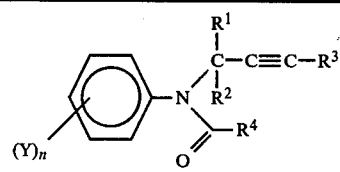

| Ex. No. | mp(bp) | Elemental Analysis - calculated (found) | | | | |
|---|---|---|---|---|---|---|
| | | C | H | Cl | N | O |
| 1 | 100–4° | 75.87(75.36) | 5.97(6.02) | | 5.53(6.07) | 12.63(13.33) |
| 2 | 59–61° | 72.70(73.07) | 7.41(7.53) | | 6.06(5.95) | 13.83(13.81) |
| 3 | 85–92° | 76.84(76.30) | 6.81(6.76) | | 4.98(5.62) | 11.37(12.01) |
| 4 | 73–4° | 74.10(74.17) | 8.16(8.19) | | 5.40(5.88) | 12.34(12.09) |
| 5 | 90–93° | 75.87(75.53) | 5.97(6.15) | | 5.53(5.36) | 12.63(13.18) |
| 6 | 70–75° | 72.70(71.10) | 7.41(7.59) | | 6.06(5.82) | 13.83(16.71) |
| 7 | oil | 78.91(75.82) | 7.95(7.69) | | 6.13(5.58) | 7.01(9.82) |
| 8 | 105–107° | 75.87(74.79) | 5.97(6.11) | | 5.53(5.17) | 12.63(13.03) |
| 9 | oil | 72.70(72.26) | 7.41(7.53) | | 6.06(6.08) | 13.83(13.85) |
| 10 | oil | 73.95(78.91) | 7.65(7.95) | | 5.52(6.13) | 10.74(7.01) |
| 11. | 75–77° | 82.10(81.73) | 6.51(6.57) | | 5.32(5.65) | 6.07(6.60) |
| 12. | 100–102° | 76.38(76.11) | 6.41(6.62) | | 5.24(5.16) | 11.97(12.56) |
| 13. | 74–76° | 73.44(74.07) | 7.81(8.21) | | 5.71(5.79) | 13.04(13.26) |
| 14. | 68–70° | 79.63(80.12) | 7.94(8.35) | | 5.80(5.80) | 6.63(7.02) |
| 15. | 89–91° | 82.28(82.56) | 6.90(7.24) | | 5.05(5.02) | 5.77(6.17) |
| 16. | 87–89° | 79.26(79.20) | 7.54(7.63) | | 6.16(6.14) | 7.04(7.52) |
| 17. | oil | 71.87(71.13) | 6.96(7.34) | | 6.45(7.03) | 14.73(15.70) |
| 18. | 88–89° | 75.30(75.24) | 5.48(5.50) | | 5.85(6.36) | 13.37(13.58) |
| 19. | 72–74° | 79.26(79.28) | 7.54(7.69) | | 6.16(6.58) | 7.04(7.50) |

The N-substituted alkynyl anilines of this invention are systemic/eradicant fungicides which possess a high degree of activity against phytopathogenic fungi especially Oömycetes. The compounds of this invention are particularly effective in controlling Oömycetes at rates of application of less than 2000 ppm. The compounds to be tested were diluted in absolute methanol so that 1 ml of the dilution added to 49 ml of potato dextrose agar equaled 1,000 ppm. Twenty ml of the agar treated with the compound to be tested was added to a plastic petri plate and the plate was inoculated with a 6 mm diameter plug of a 4 day culture of *Pythium ultimum*. After 72 hours, the radial growth of the fungus was observed.

This test showed that *P. ultimum* did not grow on potato dextrose agar that contained 1,000 ppm of the experimental fungicides.

Phytopathogenic fungi which are controlled at rates of application of less than 2000 ppm by the compounds of this invention include bean powdery mildew (*Erysiphe polygoni*) on bean plants, grape downy mildew (*Plasmopora viticola*) on grape seedlings, and tomato late blight (*Phytophthora infestans*) on tomato seedlings.

Methods for evaluating compounds for activity against phytopathogenic fungi are well known in the art. One method utilized in evaluating the compounds of this invention involves a preliminary fungicidal evaluation which is carried out using the compounds to be tested at a rate of application of 300 ppm and spraying the plants to run off with the compound in a carrier volume of about 150 gallons/acre.

The general procedure is to take potted plants in proper condition of growth for susceptibility to the fungal disease to be evaluated, to spray these plants on a moving belt with the compound to be tested and allow them to dry. The proper plants are then inoculated with the designated fungal spores and then allowed to incubate until the disease has developed and the percent control is read or estimated.

The following test methods are employed in evaluating the fungicidal activity of the compounds.

EXAMPLE A-Bean Powdery Mildew (*Erysiphe polygoni*)

Bean plants (var. Dwarf Hort) are thinned to two plants per pot 24 hours prior to chemical application. Bean plants are inoculated by spraying the leaves and stems with inoculum until a uniform film of inoculum is observed on the plant. Inoculated plants are maintained under existing greenhouse conditions. Treatment comparisons are made 8 to 10 days after inoculation. Typical bean powdery mildew symptoms are circular white mycelial mats (fructifications) on the leaf surface. Certain of the preferred compounds of this invention demonstrate complete control over *Erysiphe polygoni* at application rates greater than 300 ppm.

EXAMPLE B-Grape Downy Mildew (*Plasmopora viticola*)

Grape seedlings (var. Siebel 1000) 4–5 inches tall are used. *Plasmopora viticola* is cultured on grape leaves for 7 days at 65°–75° F. in a growth room at moderate light intensity, and then placed into a 70°–75° humidity cabinet for 24 hours to obtain abundant sporulation on the undersurface of the grape leaves. Leaves containing heavy levels of downy mildew infection are harvested and placed into a widemouth screwtop quart jar or similar container. Deionized water is added to the container and the container is shaken to free the spores. The resulting spore suspension is filtered through cheesecloth to remove plant debris and adjusted to a concentration of 100–125,000 spores per ml. The grape plants are inoculated by spraying the leaves with a hand held air brush until small uniform droplets of inoculum are observed on the leaves. The inoculated plants are incubated in a humid environment at 65°–70° F. for 48 hours prior to being placed in a growth room. Treatment comparisons are made 7 days after inoculation. Typical grape downy mildew symptoms appear on the upper leaf surface as pale-yellow spots variable in size and form, frequently circular without a distinct line of demarcation. Under humid conditions the lower leaf surface is covered by conspicuous fungal growth. Certain of the preferred compounds of this invention possess complete control over *Plasmopora viticola* at application rates of 300 ppm.

EXAMPLE C-Tomato Late Blight (*Phytophthora infestans*)

Tomato (var. Rutgers) seedlings, 2.5–3 inches tall, are fertilized with a water soluble fertilizer 4 to 5 days prior to chemical application to promote rapid succulent growth and better symptom expression. The spore suspension is applied with a DeVilbiss atomizer at 8 to 10 psi air pressure onto the leaf undersurface until fine droplets are formed. Inoculated seedlings are placed in a humid environment at 60°–62° F. for 40 to 45 hours, prior to being placed in the greenhouse at 70°–75° F. Treatment comparison are made 5 to 6 days after inoculation. Initially, typical tomato late blight symptoms appear as irregular, greenish-black, water-soaked patches which enlarge and become brown, with a firm corrugated surface. Severe infection will resemble frost damage. Certain of the preferred compounds of the present invention possess complete control over *Phytophthora infestans* at application rates of 300 ppm.

The N-substituted alkynyl anilines of the present invention are useful as agricultural fungicides and as such can be applied to various loci such as the seed, the soil or the foliage. For such purposes these compounds can be used in the technical or pure form as prepared, as solutions or as formulations. The compounds are usually taken up in an agronomically acceptable carrier or are formulated so as to render them suitable for subsequent dissemination as fungicides. For example, these chemical agents can be formulated as wettable powders, emulsifiable concentrates, dusts, granular formulations, aerosols, or flowable emulsion concentrates. In such formulations, the compounds are extended with an agronomically acceptable liquid or solid carrier and, when desired, suitable surfactants are incorporated.

By the term "agronomically acceptable carrier" is meant any substance which can be utilized to dissolve, disperse, or diffuse the chemical agent incorporated therein without impairing the effectiveness of the chemical agent and which does no permanent damage to such environment as the soil, the equipment and the agronomic crops.

It is usually desirable, particularly in the case of foliar spray formulations, to include adjuvants, such as wetting agents, spreading agents, dispersing agents, stickers, adhesives and the like in accordance with the agricultural practices. Such adjuvants commonly used in the art can be found in the John W. McCutcheon, Inc. publication "Detergents and Emulsifiers, Annual."

In general, the compounds of this invention can be dissolved in certain solvents such as acetone, methanol, ethanol, dimethylformamide, pyridine or dimethyl sulfoxide and such solutions can be extended with water. The concentrations of the solution can vary from about 1% to about 90% with a preferred range being from about 5% to about 50%.

For the preparation of emulsifiable concentrates, the compound can be dissolved in suitable organic solvents, or a mixture of solvents, together with an emulsifying agent which permits dispersion of the fungicide in water. The concentration of the active ingredient in emulsifiable concentrates is usually from about 10% to about 90% and in flowable emulsion concentrates, this can be as high as about 75%.

Wettable powders suitable for spraying, can be prepared by admixing the compounds with a finely divided solid, such as clays, inorganic silicates and carbonates, and silicas and incorporating wetting agents, sticking agents, and/or dispersing agents in such mixtures. The concentration of active ingredients in such formulations is usually in the range of from about 20% to about 98%, preferably from about 40% to about 75%. A typical wettable powder is made by blending 50 parts of N-(2-methoxyacetyl)-N-(2-propynyl)-2,6-dimethylbenzeneamine, 45 parts of a synthetic precipitated hydrated silicon dioxide sold under the trademark Hi-Sil®, and 5 parts of sodium lignosulfonate. In another preparation a kaolin type (Barden) clay is used in place of the Hi-Sil in the above wettable powder, and in another such preparation 25% of the Hi-Sil is replaced with a synthetic sodium silico aluminate sold under the trademark Zeolex®7.

Dusts are prepared by mixing the N-substituted alkynyl anilines with finely divided inert solids which can be organic or inorganic in nature. Materials useful for this purpose include botanical flours, silicas, silicates, carbonates and clays. One convenient method of preparing a dust is to dilute a wettable powder with a finely divided carrier. Dust concentrates containing from about 20% to about 80% of the active ingredient are commonly made and are subsequently diluted to from about 1% to about 10% use concentration.

The compounds of this invention can be applied as fungicidal sprays by methods commonly employed, such as conventional high-gallonage hydraulic sprays, low-gallonage sprays, air-blast spray, aerial sprays and dusts. The dilution and rate of application will depend upon the type of equipment employed, the method of application and diseases to be controlled, but the preferred effective amount is usually from about 0.1 lb. to about 50 lbs. per acre of the active ingredient.

As a seed protectant, the amount of toxicant coated on the seed is usually at a dosage rate of from about 0.1 to about 20 ounces per hundred pounds of seed. As a soil fungicide the chemical can be incorporated in the soil or applied to the surface usually at a rate of from about 0.1 to about 50 lbs. per acre. As a foliar fungicide, the toxicant is usually applied to growing plants at a rate of from about 0.25 to about 10 lbs. per acre.

Fungicides which can be combined with the fungicides of this invention include:

(a) dithiocarbamate and derivatives such as: ferric dimethyldithiocarbamate (ferbam), zinc dimethyldithiocarbamate (ziram), manganese ethylenebisdithiocarbamate (maneb) and its coordination product with zinc ion (mancozeb), zinc ethylenebisdithiocarbamate (zineb), zinc propylenebisdithiocarbamate (propineb), sodium methyldithiocarbamate (metham), tetramethylthiuram disulfide (thiram), the complex of zineb and polyethylene thiuram disulfide, 3,5-dimethyl-1,3,5-2H-tetrahydrothiadiazine-2-thione (dazomet); and mixtures of these and mixtures with copper salts;

(b) nitrophenol derivatives such as: dinitro(1-methylheptyl) phenyl crotonate (dinocap), 2-sec-butyl-4,6-dinitrophenyl 3,3-dimethylacrylate (binapacryl), and 2-sec-butyl-4,6-dinitrophenyl isopropyl carbonate;

(c) heterocyclic structures such as: N-trichloromethylthiotetrahydrophthalimide (captan), N-trichloromethylthiophthalimide (folpet), 2-heptadecyl-2-imidazole acetate (glyodine), 2-octylisothiazol-3-one, 2,4-dichloro-6-(o-chloroanilino)-s-triazine, diethyl phthalimidophosphorothioate, 4-butyl-1,2,4-triazole, 5-amino-1-bis(dimethylamino)-phosphinyl-3-phenyl-1,2,4-triazole, 5-ethoxy-3-trichloromethyl-1,2,4-thiadiazole, 2,3-dicyano-1,4-dithiaanthraquinone (dithianon), 2-thio-1,3-dithio-4,5-b quinoxaline (thioquinox), methyl 1-(butylcarbamoyl)-2-benzimidazole carbamate (benomyl), methyl benzimidazol-2-ylcarbamate (carbendazim), 2-(4′-thiazolyl) benzimidazole (thiabendazole), 4-(2-chlorophenylhydrazono)-3-methyl-5-isoxazolone, pyridine-2-thiol-1-oxide, 8-hydroxyquinoline sulfate and metal salts thereof; 2,3-dihydro-5-carboxanilido-6-methyl-1,4-oxathiin-4,4-dioxide-2,3-dihydro-5-carboxanilido-6-methyl-1,4-oxathiin, α-(phenyl)-(2,4-dichlorophenyl)-5-pyrimidinyl-methanol (triarimol), cis-N-(1,1,2,2-tetrachloroethyl) thio-4-cyclohexene-1,2-dicarboxyimide, 3-2-(3,5-dimethyl-2-oxycyclohexyl-2-hydroxyglutarimide (cycloheximide), dehydroacetic acid, N-(1,1,2,2-tetrachloroethylthio)-3a,4,7,7a-tetrahydrophthalimide (captafol), 5-butyl-2-ethylamino-4-hydroxy-6-methylpyrimidine(ethirimol), acetate of 4-cyclododecyl-2,6-dimethylmorpholine (dodemorph), and 6-methyl-2-oxo-1,3-dithiolo 4,5-b-quinoxaline (quinomethionate).

(d) miscellaneous halogenated fungicides such as: tetrachloro-p-benzoquinone (chloranil), 2,3-dichloro-1,4-naphthoquinone (dichlone), 2,3-dichloro-2,5-dimethoxybenzene (chloroneb), 3,5,6-trichloro-o-anisic acid (tricamba), 2,4,5,6-tetrachloroisophthalo nitrile (TCPN), 2,6-dichloro-4-nitroaniline (dichloran), 2-chloro-1-nitropropane, polychloronitrobenzenes such as: pentachloronitrobenzene (PCNB) and tetrafluorodichloroacetone;

(e) fungicidal antibiotics such as: griseofulvin, kasugamycin and streptomycin;

(f) copper-based fungicides such as: cuprous oxide, basic cupric chloride, basic copper carbonate, copper naphthenate and Bordeaux mixture; and (g) miscellaneous fungicides such as: diphenyl, dodecylguanidine acetate (dodine), phenylmercuric acetate, N-ethylmercuri-1,2,3,6-tetrahydro-3,6-endomethano-3,4,5,6,7,7-hexachlorophthalimide, phenylmercuric mono-ethanol ammonium lactate, p-dimethylamino-benzenediazo sodium sulfonate, methyl iso-thiacyanate, 1-thiocyano-2,4-di-nitrobenzene, 1-phenylthiosemicarbazide, nickel-containing compounds, calcium cyanamide, lime sulfur, sulfur, and 1,2-bis(3-methoxycarbonyl-2-thioureido) benzene (thiophanatemethyl).

The compounds of this invention can be advantageously employed in various ways. Since these compounds possess systemic/eradicant fungicidal activity, they can be employed in the storage of cereal grain. These compounds can also be employed as fungicides in turf, fruit orchards, vegetables and golf course applications. Other applications of the compounds of this invention will suggest themselves to those skilled in the art of agriculture and horticulture.

I claim:

1. A compound according to the formula

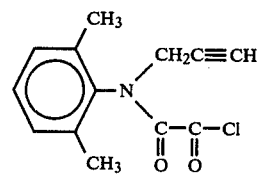

2. A compound having the formula

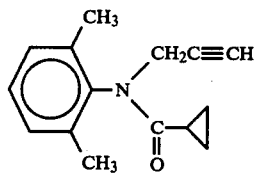

3. A fungicidal composition which comprises an agronomically acceptable carrier, and, as the active ingredient, a compound according to the formula

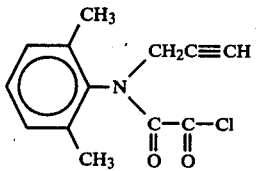

4. A fungicidal composition which comprises an agronomically acceptable carrier, and, as the active ingredient, a compound of the formula

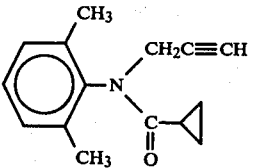

5. A method for controlling phytopathogenic fungi in agronomic crops which comprises applying to the plant, the plant seed, or the plant habitat, a fungicidally effective amount of a compound of the formula

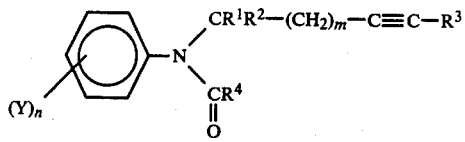

wherein $R^1$, $R^2$ and $R^3$ are independently hydrogen, $(C_1-C_4)$ alkyl, $(C_2-C_4)$alkenyl, $(C_2-C_4)$alkynyl, $(C_3-C_8)$cycloalkyl, $(C_5-C_8)$cycloalkenyl, halogen, cyano, carbo$(C_1-C_{10})$alkoxy, or aryl or aryl$(C_1-C_4)$alkyl the aryl portion of which is optionally substituted;

$R^4$ is $(C_3-C_8)$ cycloalkyl, $(C_5-C_8)$cycloalkenyl, mono or di$(C_1-C_6)$alkylamino$(C_1-C_4)$alkyl, mono or di$(C_2-C_6)$alkenylamino$(C_1-C_4)$alkyl, mono or di$(C_2-C_6)$alkynylamino$(C_1-C_4)$alkyl, or halocarbonyl;

Y is halogen, $(C_1-C_4)$alkyl, $(C_1-C_4)$alkoxy, nitro, mono or di$(C_1-C_4)$alkylamino, trihalomethyl, cyano, phenyl, phenoxy, phenylthio, phenylsulfinyl, or phenylsulfonyl, the aryl portion of which is optionally substituted; and m and n are independently zero or an integer from 1 to 3.

6. The method of claim 5 wherein $R^1$, $R^2$ and $R^3$ are independently hydrogen or $(C_1-C_4)$alkyl;

$R^4$ is cyclopropyl, cyclopentyl, cyclohexyl, cyclohexenyl, methylaminomethyl, dimethylaminomethyl, ethylaminomethyl, diethylaminomethyl, aryloxymethyl, allylaminomethyl, propargylaminomethyl, or chlorocarbonyl;

Y is halogen, $(C_1-C_4)$alkyl, $(C_1-C_4)$alkoxy, nitro, trifluoromethyl, phenyl, phenoxy, phenylthio, phenylsulfinyl, or phenylsulfonyl wherein the phenyl portion of a Y substituent is optionally substituted with up to two halogen atoms, methyl, methoxy, nitro or trifluoromethyl groups;

m is 0; and n is 0 or the integer 1 or 2.

7. The method of claim 6 wherein $R^1$, $R^2$ and $R^3$ are hydrogen; $R^4$ is cyclopropyl, or chlorocarbonyl, Y is methyl or ethyl and m is zero.

8. A method for controlling phytopathogenic fungi in agronomic crops which comprises applying to the plant, the plant seed, or the plant habitat, a fungicidally effective amount of a composition according to claims 3 or 4.

* * * * *